United States Patent [19]

Malz, Jr. et al.

[11] Patent Number: 4,814,444

[45] Date of Patent: Mar. 21, 1989

[54] PROCESS FOR THE SELECTIVE REDUCTION OF 2-HYDROXYQUINOXALINE-4-OXIDES

[75] Inventors: Russell E. Malz, Jr., Naugatuck; John W. Sargent, Waterbury; Joseph A. Feiccabrino, Naugatuck, all of Conn.

[73] Assignee: Uniroyal Chemical Company, Inc., Middlebury, Conn.

[21] Appl. No.: 64,908

[22] Filed: Jun. 19, 1987

[51] Int. Cl.$^4$ .................... C07D 241/44; B01J 27/45; C07B 35/2

[52] U.S. Cl. ..................... 544/354; 502/223; 564/200

[58] Field of Search ............... 544/354, 353; 502/223

[56] References Cited

U.S. PATENT DOCUMENTS

| | | | |
|---|---|---|---|
| 3,350,450 | 10/1967 | Dovell et al. | 260/577 |
| 4,620,003 | 10/1986 | Ishikura | 544/354 |
| 4,636,562 | 1/1987 | Davis | 544/354 |

FOREIGN PATENT DOCUMENTS 48973 3/1982 Japan .

158184 8/1985 Japan .................... 544/354

OTHER PUBLICATIONS

Japan Abstract for JP 158184 (8/19/85).
Derwent Abstract #85-240373/39 for JP 158184 (8/19/85).
Dovell et al., *J. Am. Chem. Soc.* 87 p. 2767 (1965).
"Engelhard Catalysts and Precious Metal Chemicals Catalog", pp. 211 and 215 (1985).
Sakata et al, "The Facile One Pot Synthesis of 6-Substituted 2(1H)-Quinoxalinones", *Heterocycles*, vol. 23, No. 1 (1985).
Elina et al, "N-Oxides of the Quinoxaline Series", *Zhurnal Obshchei Khimii*, vol. 33, No. 5, pp. 1544–1551.

*Primary Examiner*—Mark L. Berch
*Assistant Examiner*—E. Bernhardt
*Attorney, Agent, or Firm*—Raymond D. Thompson

[57] ABSTRACT

Certain 2-quinoxalinol-4-oxides are selectively reduced to form 2-quinoxalinols employing hydrogen as a reducing agent by reacting such 2-quinoxalinol-4-oxides with a catalyst selected from the group consisting of sulfided platinum, sulfided palladium, sulfided rhodium and sulfided ruthenium.

13 Claims, No Drawings

PROCESS FOR THE SELECTIVE REDUCTION OF 2-HYDROXYQUINOXALINE-4-OXIDES

FIELD OF THE INVENTION

This invention is directed to an improved process for the selective reduction of certain 2-quinoxalinol-4-oxides to form 2-quinoxalinols employing a catalyst selected from the group consisting of sulfided platinum, sulfided rhodium, sulfided ruthenium and sulfided palladium and employing hydrogen as the reducing agent.

BACKGROUND OF THE INVENTION 2-quinoxalinol compounds, such as 6-chloro-2-hydroxyquinoxaline, are well known intermediates for the production of pharmaceutically and agriculturally effective chemicals. These compounds are generally prepared by the selective reduction of 2-quinoxalinol-4-oxides. Selective reduction is necessary so that excessive reduction, resulting in the formation of compounds such as 3,4-dihydro-2-quinoxalinol, can be avoided. This is particularly a problem with halogenated 2-quinoxalinol compounds wherein excessive hydrogenation will eliminate the halogen substituent.

U.S. Pat. No. 4,620,003 to Ishikura discloses a process for the reduction of 2-quinoxalinol-4-oxide compounds to 2-quinoxinol compounds, which process involves reacting a 2-quinoxalinol-4-oxide with hydrazine in the presence of (i) a Raney catalyst (especially Raney nickel or sulfided Raney nickel) and (ii) a alkali metal hydroxide, an alkaline earth metal hydroxide, or ammonium hydroxide. While this process reduces the 2-quinoxalinol-4-oxides in desirable efficiencies, a major drawback in the commercial use of the Ishikura process is the relatively high cost of hydrazine relative to other potential reducing agents, in particular hydrogen.

While U.S. Pat. No. 4,636,562 to Davis discloses a process for preparing 2-chloro-6-haloquinoxaline compounds from the corresponding 4-halo-2-nitroaniline, which process includes a step involving the reduction of 6-chloro-2-hydroxyquinoline-4-oxide to 6-chloro-2-hydroxyquinoline employing hydrogen as a reducing agent (in the presence of an aqueous alkali metal hydroxide solvent and a transition element metal hydrogenation catalyst, preferably Raney nickel), this Davis process is also not desirably commercialized. This is because Davis indicates that hydrogen pressures of 1-4 atmospheres are effective with pressures of 1-2 atmospheres being preferred. It is well known to those of ordinary skill in the art that processes involving gaseous hydrogen at such low pressures are inherently dangerous because there is a risk of air leaking into the system. If hydrogen and oxygen contact the hydrogenation catalyst together, water is formed in an explosive manner.

Sakata et al, "The Facile One Pot Synthesis of 6-Substituted 2(1H)-quinoxalinones", Heterocycles, Vol. 23, No. 1 (1985), disclose a process for the reduction of 6-chloro-2-quinoxalinol-4-oxide to 6-chloro-2-quinoxalinol employing hydrogen as a reducing agent and palladium as a catalyst. However, Sakata et al indicate that an undesirable amount of overly reduced by-product is formed.

Consequently, it would be desirable to possess a process for the selective reduction of 2-quinoxalinol-4-oxides to 2-quinoxalinols safely and efficiently employing hydrogen as a reducing agent.

Accordingly, it is an object of this invention to provide a method of selectively reducing 2-quinoxalinol-4-oxides to 2-quinoxalinols employing hydrogen as a reducing agent.

It is a further object of this invention to provide a high pressure method of selectively reducing 2-quinoxalinol-4-oxides to 2-quinoxalinols employing hydrogen as a reducing agent such that the danger of air leaking into the system is minimized.

The above objects and additional objects will become more fully apparent from the following description and accompanying examples.

DESCRIPTION OF THE INVENTION

The present invention is directed to a process for preparing a 2-quinoxalinol compound of the formula:

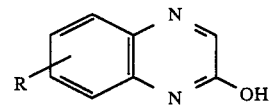

wherein R is hydrogen, halogen or trihalomethyl; which process comprises reducing a 2-quinoxalinol-4-oxide compound of the formula:

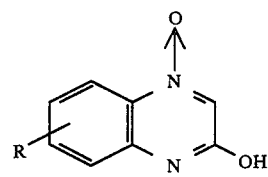

wherein R is as defined above, with hydrogen in the presence of a catalytically effective amount of at least one catalyst selected from the group consisting of sulfided platinum, sulfided palladium, sulfided rhodium and sulfided ruthenium.

The 2-quinoxalinol-4-oxide compounds employed as starting materials in the process of this invention are of the formula:

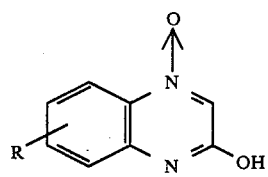

wherein R is hydrogen, halogen or trihalomethyl. Preferably, R is hydrogen, chlorine, fluorine, trichloromethyl or trifluoromethyl. A particularly preferred starting material is 6-chloro-2-hydroxyquinoxaline-4-oxide, which is subsequently reduced to 6-chloro-2-hydroxyquinoxaline.

These starting materials may be in isolated form or may be present as a reaction product. Thus, for example, 6-chloro-2-hydroxyquinoxaline-4-oxide may be present as the product of the reaction of 4-chloro-2-nitroacetoacetanilide with a hydroxide (such as sodium hydroxide or potassium hydroxide).

The process of this invention is catalyzed by a hydrogenation catalyst selected from the groups consisting of sulfided platinum, sulfided palladium, sulfided rhodium and sulfided ruthenium. Most preferably, sulfided platinum is employed. Such catalysts are typically employed in amounts of about 0.5 to 100 parts by weight per 100 parts by weight of 2-quinoxalinol-4-oxide.

When the starting material employed in the process of this invention is the reaction product of a nitroacetoacetanilide and a hydroxide, the reaction of this invention is conducted in a solution containing at least one compound selected from the group consisting of alkali metal hydroxides, alkaline earth metal hydroxides and ammonium hydroxide. Water is preferred as a reaction solvent but organic solvents (such as alcohols or hydrocarbons) or solvent mixtures of water with an organic solvent may also be employed.

The process of this invention is typically carried out at pressures between about 3 and about 100 atmospheres, with pressures of between about 6 and about 60 atmospheres being preferably employed. Reaction temperature may vary widely, with temperatures typically ranging between about 10° and about 90° C, and preferably ranging between about 20° and about 75° C.

been produced by the reaction of 482.4 grams of 4-chloronitroacetoacetanilide with 813 grams of 86.9 percent potassium hydroxide in a 3200 grams of water) in a 17.6 weight percent aqueous potassium hydroxide solution. The amount and type of catyst indicated in Table I below was added and the autoclave sealed. In this regard, it is to be noted that, with the exception of Comparative Experiment B (NiS), all catalysts were 5 weight percent on carbon. The autoclave was purged, first with nitrogen and subsequently with hydrogen. Hydrogen was added until the pressure was as indicated in Table I below. The autoclave was heated with agitation for the indicated reaction time, and was then cooled and depressurized. The reaction product was removed with water, filtered through celite (to remove catalyst), and dried. The reaction product was analyzed, and the yield (based upon the complete cyclization, reduction, neutralization, filtration and drying steps) calculated. The results of such analyses are presented in Table I.

TABLE I

Reduction of 6-Chloro-2-Hydroxyquinoline-4-oxide to 6-Chloro-2-Hydroxyquinoline Employing $H_2$ as the Reducing Agent

| Example or Comparative Experiment | Catalyst Type | Catalyst Amount (g) | Reaction Temperature (°C.) | Reaction Pressure (psig) | Reaction Time (hours) | Percent $H_2$ Absorped* | Percent Yield** |
|---|---|---|---|---|---|---|---|
| 1 | Sulfided Pt | 0.125 | 60 | 100–200 | 5.0 | 100 | 79 |
| 2 | Sulfided Pt | 0.125 | 60 | 100–200 | 4.0 | 100 | 78 |
| 3 | Sulfided Pd | 1.9 | 20 | 100–200 | 5.8 | 117 | 43 |
| 4 | Sulfided Rh | 2.0 | 20 | 600–700 | 2.0 | 114 | 61 |
| 5 | Sulfided Ru | 1.9 | 60 | 620–720 | 5.9 | 157 | 24 |
| A | Pd | 1.0 | 30 | 450–700 | 0.08 | 232 | <0.5 |
| B | Sulfided Ni | 3.8 | 60 | 660–760 | 5.0 | 113 | 19 |

*Point at which $H_2$ absorption had essentially ceased.
**Based upon molar conversion of 4-chloronitroacetoacetanilide into 6-chloro-2-hydroxyquinoline.

The reaction temperatures and pressures which are most preferably employed will vary in accordance with a number of factors including the particular catalyst selected; the starting material employed: the catalyst concentration; and the like. As is apparent to one skilled in the art, reaction pressures and temperatures which are too high will reduce the selectivity of the reaction and produce products which may be too greatly reduced. Conversely, reaction temperatures and pressures which are too low will reduce the activity of the catalyst. However, one of ordinary skill in the art may readily determine the optimum reaction conditions for a particular set of reactants by routine experimentation.

By employing methods well known to those skilled in the hydrogenation art, the process of this invention may be employed in a continuous or in a batch manner.

Because the process of this invention employs hydrogen as a reducing agent, it is greatly more economical than prior art processes employing relatively expensive chemicals (such as hydrazine) as reducing agents. Moreover, because the process of this invention may be run at high pressures, the danger of an explosion occurring due to the leaking in of air is greatly reduced.

EXAMPLES

The following Examples are intended to further illustrate the invention and are not intended to limit the scope of the invention in any manner whatsoever.

EXAMPLES 1–5 and Comparative Experiments A and B

To a 300 ml autoclave containing agitation means was added 125 ml of a stock solution containing 9.2 grams of 6-chloro-2-hydroxyquinoxaline-4-oxide (which had The above data indicate the unexpectedly improved yield of selectively reduced product achieved by the process of this invention which employs a sulfided platinum, sulfided palladium, sulfided rhodium or sulfided ruthenium catalyst relative to catalysts of the type or similar to the type employed in the prior art.

It should be recognized that certain combinations of increased pressure and temperature should be avoided in the practice of the present invention, as the use of sulfided palladium at a reaction temperature of 60° C. and a reaction pressure of 500–700 psig produced a product where excessive reduction had occurred.

What is claimed is:

1. A process for preparing a 2-quinoxalinol compound of the formula:

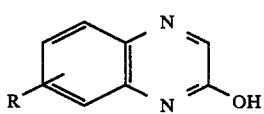

wherein R is hydrogen, halogen or trihalomethyl; which process comprises reducing a 2-quinoxalinol-4-oxide compound of the formula:

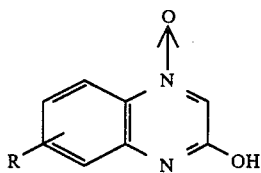

wherein R is as defined above, with hydrogen in the presence of a catalytically effective amount of a catalyst selected from the group consisting of sulfided platinum, sulfided palladium and sulfided rhodium.

2. A process in accordance with claim 1 wherein said 2-quinoxalinol-4-oxide is in a solution further comprising a compound selected from the group consisting of alkali metal hydroxides, alkaline earth metal hydroxides and ammonium hydroxide.

3. A process in accordance with claim 2 wherein said solution is an aqueous solution.

4. A process in accordance with claim 1 wherein R is selected from the group consisting of hydrogen, chlorine, fluorine, trichloromethyl and trifluoromethyl.

5. A process in accordance with claim 1 wherein the starting material is 6-chloro-2-hydroxyquinoline-4-oxide.

6. A process in accordance with claim 1 wherein the reduction takes place at between about 10° and about 90° C.

7. A process in accordance with claim 6 wherein the reduction takes place at between about 20° and about 75° C.

8. A process in accordance with claim 1 wherein the reduction takes place at a pressure of between about 3 and about 100 atmospheres.

9. A process in accordance with claim 8 wherein the reduction takes place at between about 6 and about 60 atmospheres.

10. A process in accordance with claim 1 wherein the catalyst is sulfided platinum.

11. A process for preparing 6-chloro-2-hydroxyquinoline from 6-chloro-2-hydroxyquinoline-4-oxide which process reacting 6-chloro-2-hydroxyquinoline-4-oxide with hydrogen in the presence of (a) a catalytically effective amount of sulfided platinum and (b) an aqueous solution of an alkali metal hydroxide at between about 10° and about 90° C. and at between about 3 and about 100 atmospheres.

12. A process in accordance with claim 11 wherein such reaction occurs at between about 20° and about 75° C. and at between about 6 and about 60 atmospheres.

13. A process in accordance with claim 11 wherein said reaction occurs at about 60° C. and at between about 8 and about 15 atmospheres.

* * * * *